US00PP10913P

United States Patent [19]

Evison et al.

[11] Patent Number: Plant 10,913

[45] Date of Patent: May 25, 1999

[54] CLEMATIS PLANT NAMED 'EVIFIVE'

[75] Inventors: Raymond J. Evison, Guernsey, United Kingdom; Mogens N. Olesen, Fredensborg, Denmark

[73] Assignee: Poulsen Roser International, SARL, Souvans, France

[21] Appl. No.: 08/926,908

[22] Filed: Sep. 10, 1997

[51] Int. Cl.[6] ..... A01H 5/00

[52] U.S. Cl. ..... Plt./54.1

[58] Field of Search ..... Plt./54.1

*Primary Examiner*—Elizabeth C. Kemmerer

[57] ABSTRACT

A new large-flowered Clematis cultivar which produces violet purple flowers with a dark red central stripe and yellow anthers. The variety is compact, climbing, clinging and suitable for patio container growth. The variety successfully propagates from softwood cuttings and is suitable for ornamental use in outdoor settings in a variety of climatic conditions. This new and distinct variety has shown to be uniform and stable in the resulting generations from propagation.

2 Drawing Sheets

SUMMARY OF THE DISCOVERY

The present discovery constitutes a new and distinct variety of Clematis which originated from a controlled crossing between two unnamed seedlings and was discovered in a cultivated area.

The two parents were crossed and the resulting seed was planted in a controlled environment. The new variety is named 'EVIfive'.

The objective of the hybridization of this Clematis variety for the nursery industry was to create a new and distinct variety with unique qualities:

1. Large, distinctly colored flowers
2. Orderly plant habit
3. Compact growth and flowering habit, making it suitable for patio container growth.

These qualities required improvement in Clematis varieties that were in commercial cultivation and the objectives have been substantially achieved in the new variety, as evidenced by the unique combination of characteristics that are present in 'EVIfive' which distinguish it from all other varieties of which we are aware.

Seedlings from the hybridization were evaluated in a controlled environment. 'EVIfive' was selected by Raymond J. Evison and Mogens N. Olesen in their Clematis development program in Domarie Vinieries Les Sauvagees, St. Sampsons, Guernsey, Channel Islands, United Kingdom in 1988.

Asexual reproduction of 'EVIfive' by cuttings was first done by Raymond J. Evison and Mogens N. Olesen in Domarie Vineries Les Sauvagees, St. Sampsons, Guernsey, Channel Islands, United Kingdom in 1990. This initial and subsequent propagations have demonstrated that the characteristics of 'EVIfive' are true to type and are transmitted from one generation to the next.

BRIEF DESCRIPTION OF THE DRAWING

The accompanying color illustrations show as true as is reasonably possible to obtain in color photographs of this type, the typical characteristics of the buds, tepals and leaves of the new variety, with different tepals shown in various stages of maturity. The tepal form, tepal counts, tepal colors, tepal buds, tepal parts, pedicels and the cultivar's foliage are depicted.

DETAILED DESCRIPTION OF THE VARIETY

The following is a detailed description of 'EVIfive', as observed in its growth throughout the flowering period in glasshouses at Domarie Vineries Les Sauvagees, St. Sampsons, Guernsey, Channel Islands, United Kingdom. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing Clematis variety is 'EVIone' a variety currently being applied for as Application Ser. No. 08/627,506. Chart 1 details several physical characteristics of the applicant and the comparison varieties.

CHART 1

| | 'EVIfive' | 'EVIone' |
|---|---|---|
| Plant Height | short, 1–3 meters | 1–3 meters |
| Leaf Main Color | RHS 137 A | Between RHS 137 B and RHS 143 A |
| Flowering Period | spring/fall | spring/fall |
| Anther Color | Yellow | Cream |
| Tepal Color (upper) | RHS 60 B | RHS 84 C |
| Plant Habit | Herbaceous | Herbaceous |

Parents: Unnamed seedling×Unnamed seedling

Classification:

*Botanical.*—Clematis L.

*Commercial.*—Early, large-flowered cultivar.

Flower and Flower Bud

Blooming habit: Recurrent.

Flower bud:

*Size.*—40–50 mm in length.

*Bud form.*—Elongated and ovoid.

*Bud color.*—Green-grey bud at ¼ opening.

*Sepals.*—None.

*Peduncle.*—Length: 110–150 mm average length. Color: Medium green. R.H.S. 143 C of the Green Group. Strength: Erect.

*Borne.*—Singly.

Flower bloom:

*Size.*—Large, 220 mm. on average.

*Form.*—Upon opening, concave, flat with tepals reflexing.

*Color.*—Upon opening, the upper surface is R.H.S. 78 A of the Purple Color Group with the central bar of the flower being 72 A of the Red Purple Color Group. Upon opening, the reverse side is green. After opening, the upper surface is R.H.S. 78 B the Purple Color Group. After opening, the reverse surface is R.H.S. 82 D of the Purple Violet Color Group. The base of the tepals is R.H.S. 72 A of the Red Purple Group. The general tonality from a distance is Pink.

*Variations.*—Red-Purple central bar R.H.S. 72 A.

*Fragrance.*—None.

*Lasting quality on plant and as a cut flower.*—Short-medium lasting.

Tepals:

*Petalage.*—Single. Average range: 6–8.

*Shape.*—Individual tepal shape is elliptic.

*Cross section.*—Slightly reflexed.

*Undulation of margin.*—Weak.

*Tepal apex.*—Broadly acute.

*Recurvature of tip.*—Slightly curved.

*Persistence.*—Drop off cleanly.

*Arrangement.*—Tepals are arranged regularly.

Reproductive organs:

*Pollen.*—Color: Cream. Abundance: Average.

*Anthers.*—Size: Medium. Color: Yellow. Arrangement: Regular.

*Filaments.*—Color: Violet.

*Stigmas.*—Central, mildly protruding.

*Styles.*—Color: Grey/Green.

*Ovaries.*—Normal.

Plant

Plant form: Climbing and spreading.

Plant growth: Average vigor.

Height: Seasons growth attains 2–2.5 meter.

Hardiness: Trials to date show the variety hardy in USDA Zones 4–9.

Stems:

*Color.*—Young wood: Green with red coloration. Older wood: Brown.

*Internodes.*—Cylindrical. Length 120–170 mm.

*Petioles.*—Incidence: Moderate. Size: Average length: 60 mm. Color: Red-green. Clasping: Clasps by leaf petiole.

Bark: Young wood: Smooth. Older wood: Rough.

Plant foliage: Deciduous. Trifoliate.

*Leaf size.*—Medium. Length 100 mm.

*Abundance.*—Average.

*Color.*—Top: Medium green. R.H.S. 137 A of the Green Color Group. Bottom: Light green. R.H.S. 137 C of the Green Color Group. New growth: Reddish green. Older growth: Red brown.

Plant leaves and leaflets:

*Stipules.*—Absent.

*Petiole.*—Length: 60 mm. Underneath: Without prickles.

*Leaf edge.*—Terminal leaflet margin is entire.

*Shape.*—Base of leaflet: Rounded. Apex of leaflet: Acute.

*Texture.*—Upper side: Glabrous. Lower side: Ribbed.

*Surface.*—Matte Finish.

Disease resistance: Subject to any disease that normally attacks the species, however the new variety is more tolerant to Mildew than some Clematis.

We claim:

1. A new and distinct cultivar of Clematis plant, substantially as herein shown and detailed, as a distinct and novel Clematis cultivar with its large violet-red striped flowers with a yellow center, which is a compact plant with symmetrical flowers making this an unique cultivar suitable for ornamental use in a wide variety of climatic conditions.

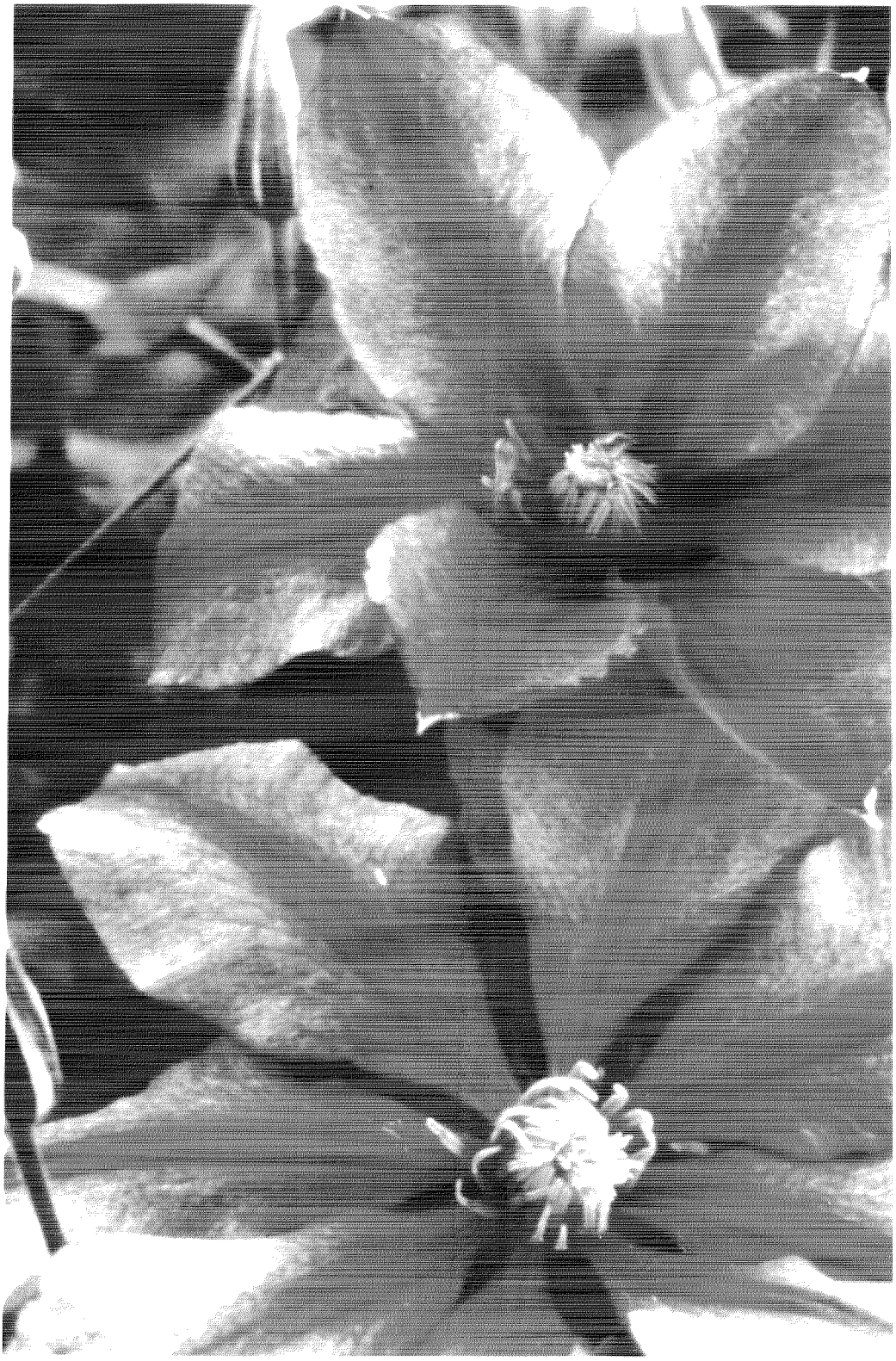

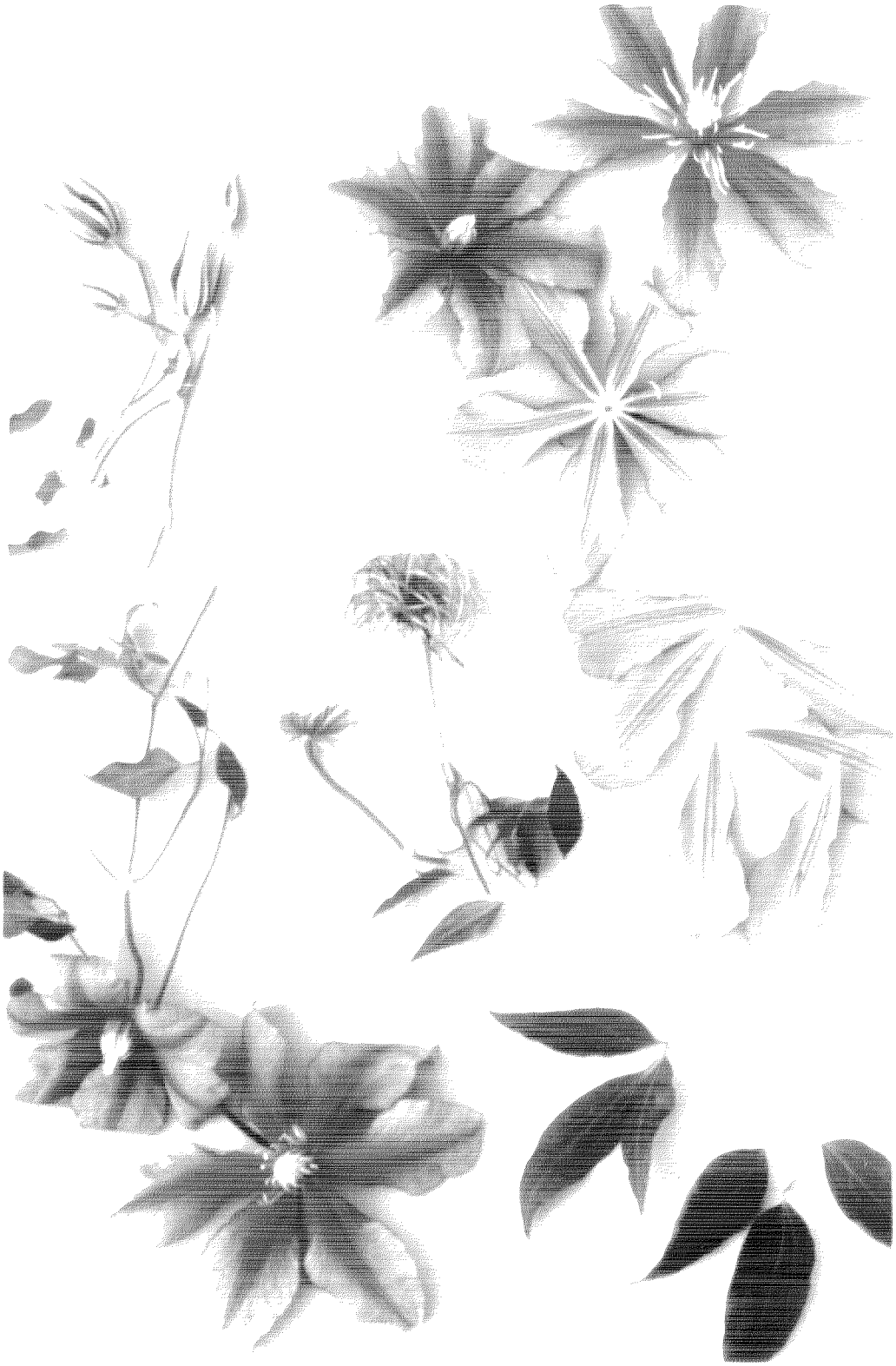

* * * * *